United States Patent [19]

Alferness

[11] Patent Number: 5,304,218
[45] Date of Patent: Apr. 19, 1994

[54] CARDIAC LEAD IMPLANTING ARRANGEMENT AND METHOD

[75] Inventor: Clifton A. Alferness, Redmond, Wash.

[73] Assignee: InControl, Inc., Redmond, Wash.

[21] Appl. No.: 892,177

[22] Filed: Jun. 2, 1992

[51] Int. Cl.$^5$ ............................................. A61N 1/05
[52] U.S. Cl. ............................................. 607/122
[58] Field of Search ............... 128/419 C, 783–786, 128/642, 419 P; 607/122–125, 131

[56] References Cited

U.S. PATENT DOCUMENTS

| | | | |
|---|---|---|---|
| 4,972,847 | 11/1990 | Dutcher et al. | 128/785 |
| 5,003,990 | 4/1991 | Osypka | 128/785 |
| 5,139,033 | 8/1992 | Everett et al. | 128/785 |

*Primary Examiner*—Lee S. Cohen
*Assistant Examiner*—Marianne Parker
*Attorney, Agent, or Firm*—Foley & Lardner

[57] ABSTRACT

An arrangement and method facilitates the implantation of an electrode of an endocardial or intravenous lead at an implantation site within the heart of a human. The arrangement includes a guide wire which is formed of flexible material and which may be fed along a predetermined path which includes the implantation site. The arrangement further includes a lead formed of flexible material which includes a proximal end, a distal end, and an electrode to be implanted. The lead further includes an integrally formed follower which slidingly engages the guide wire to permit the lead to be guided along the predetermined path until the electrode to be implanted resides at its implantation site. Thereafter, the guide wire is retracted along the predetermined path to cause the electrode to remain at its implantation site.

12 Claims, 7 Drawing Sheets

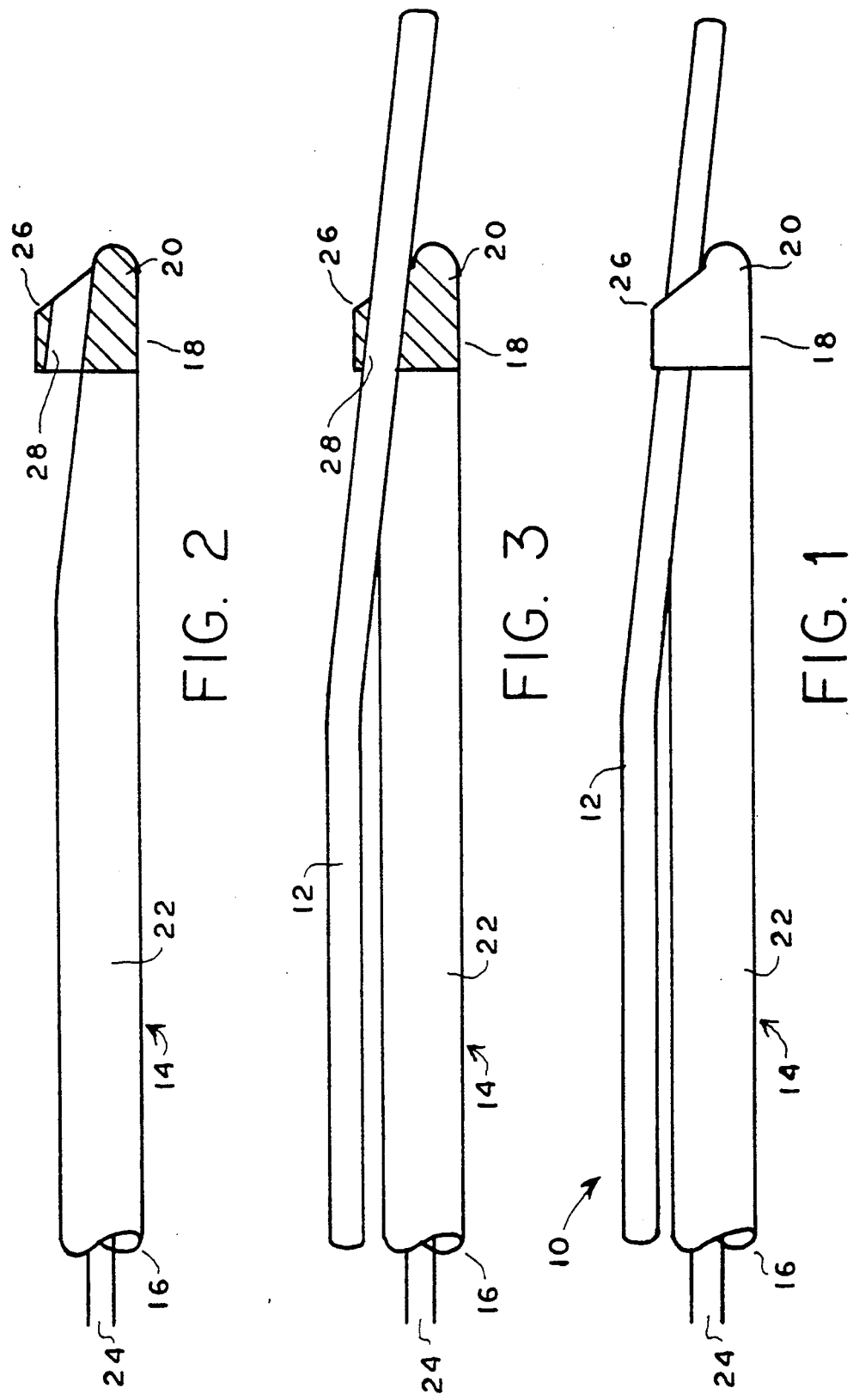

CARDIAC LEAD IMPLANTING ARRANGEMENT AND METHOD

BACKGROUND OF THE INVENTION

The present invention relates to an arrangement to facilitate the implantation of an electrode at an implantation site within the human body. The present invention is more particularly directed to such an arrangement for implanting an electrode of a cardiac lead within a coronary vein of the human heart.

The practice of implanting cardiac pacemakers or defibrillators in the body of a human patient generally includes the implantation of one or more electrodes in, on, or near the heart. Such electrodes are used to either sense heart activity or deliver pacing or cardioverting electrical energy to the heart. Often, an electrode may be utilized for both functions.

Pacemakers and defibrillators generally include electrical components including sense amplifiers, a pulse generator, and a battery which are housed within a sealed enclosure. The enclosures are generally implanted in a subcutaneous pocket usually located in the subclavicular region in adults or in the abdominal region in children.

The pacemakers or defibrillators are generally coupled to the heart through one or more leads which include the aforementioned electrodes. The leads include a proximal end having a connector which connects to a terminal of the pacer or defibrillator enclosure and a distal end which carries the electrode. Some leads may include more than one electrode. The body of a lead is generally composed of conductive wires surrounded by insulation. The conductive wires couple the lead connector to the lead electrode or electrodes.

An endocardial lead is a lead which is implanted within a chamber of the heart so that the distal electrode of the lead can be fixed to the inner wall of a heart chamber. In implanting such a lead, a transvenous approach is utilized wherein the lead is inserted into and passed through the subclavian, jugular, or cephalic vein and into the appropriate heart chamber. An intravenous lead is a lead which is implanted within a coronary vein such as the great vein. As disclosed in copending application Ser. No. 07/856,514, filed on Mar. 24, 1992, in the names of John M. Adams, Clifton A. Alferness, and Paul E. Kreyenhagen, and entitled IMPROVED ATRIAL DEFIBRILLATOR, LEAD SYSTEMS, AND METHOD, which application is assigned to the assignee of the present invention and incorporated herein by reference, such an intravenous lead is particularly useful in an implantable atrial defibrillator application. The distal end of the intravenous lead there disclosed is passed through the superior vena cava, the right atrium, the valve of the coronary sinus, the coronary sinus, and into a coronary vein communicating with the coronary sinus, such as the great vein. The intravenous lead includes a distal or tip electrode which, when residing in the aforementioned coronary vein, such as the great vein, is closely adjacent the left ventricle of the heart for sensing ventricular activity of the heart. The lead further includes an elongated proximal electrode which is spaced from the distal or tip electrode so that when the tip electrode is within the coronary vein, the proximal electrode resides in the coronary sinus above the left ventricle and closely adjacent the left atrium of the heart. The proximal electrode is utilized for both sensing atrial activity of the heart and delivering cardioverting electrical energy to the atria between the coronary sinus and another electrode within the right atrium which is carried by either the same aforementioned intravenous lead or by another lead.

Experience has shown that it is often difficult to feed an endocardial or intravenous lead along a desired predetermined path to implant the electrode or electrodes at a desired implantation site either in a chamber of the heart or in a desired vein near the heart. This is especially true for intravenous leads due to anomalies in vascular anatomy and the number of veins which may communicate with the desired feed path.

One arrangement in attempting to solve this problem is described in Osypka, U.S. Pat. No. 5,003,990. The arrangement there disclosed includes a guide wire which is fed along a desired path through an artery or vein and a carriage arranged to releasably receive the distal end of a lead or catheter and to be pushed along the guide wire for guiding the lead along the guide wire. When the lead or catheter reaches the desired position, the carriage must be removed from the lead or catheter and then retracted along the guide wire by the pulling of another wire attached to the carriage or by the retraction of the guide wire. Such retraction of the carriage presents the possibility of damage to an artery or vein by the carriage. In addition, releasing the carriage from the guide wire requires the lead or catheter to be bent in the area of the carriage presenting further possibilities of tissue damage during such carriage removal. Still further, once the lead or catheter is free of the carriage, its distal end will not be at its desired final implantation position. Still further, use of the carriage during both implantation of the lead or catheter and retraction of the carriage requires numerous manipulations by the physician which only adds further complexity to an already complex procedure.

SUMMARY OF THE INVENTION

The present invention therefore provides an improved arrangement to facilitate the implantation of an electrode of an endocardial or intravenous lead at an implantation site within the body of a human. The arrangement includes guide wire means formed of flexible material and arranged to be fed along a predetermined path within the body wherein the predetermined path includes the implantation site. The arrangement further includes lead means formed of flexible material and including a proximal end, a distal end, and the electrode to be implanted. The lead means further includes follower means integrally formed in the lead means for slidingly engaging the guide wire means. As a result, after the guide wire means is fed to extend along the predetermined path, the follower means is engaged with the guide wire means to permit the lead means to be guided along the predetermined path until the electrode to be implanted resides at the implantation site whereupon, the guide wire means is retracted along the predetermined path to cause the electrode to be implanted to remain at the implantation site.

The present invention further provides a method of implanting an electrode at an implantation site within the body of a human. The method includes the steps of providing a guide wire formed of flexible material, feeding the guide wire along a predetermined path within the body wherein the predetermined path includes the implantation site, and providing lead means formed of flexible material and including a proximal end, a distal end, the electrode to be implanted, and a follower integrally formed in the lead means for slidingly engaging the guide wire. The method further includes the steps of engaging the follower means with the guide wire and sliding the lead means on the guide wire along the predetermined path until the electrode reaches the implantation site, and thereafter, sliding the guide wire from engagement with the follower means and retracting the guide wire from the body along the predetermined path.

The present invention more particularly provides a method of implanting an electrode at an implantation site within a coronary vein communicating with the coronary sinus in the body of a human. The method includes the steps of providing a guide wire formed of flexible material, feeding the guide wire along a predetermined path within the body wherein the predetermined path includes the superior vena cava, the right atrium, the valve of coronary sinus, the coronary sinus, and the coronary vein communicating with the coronary sinus, and providing lead means formed of flexible material and including a proximal end, a distal end, the electrode to be implanted, and a follower integrally formed in the lead means for slidingly engaging the guide wire. The method further includes the steps of engaging the follower means with the guide wire and sliding the lead means on the guide wire along the predetermined path until the electrode reaches the implantation site and thereafter, sliding the guide wire from engagement with the follower means and retracting the guide wire from the body along the predetermined path.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIG. 1 is a side plan view of an arrangement to facilitate the implantation of an electrode of an endocardial or intravenous lead at an implantation site within the human heart including a guide wire and a lead having an integrally formed follower slidingly engaged with the guide wire in accordance with the present invention;

FIG. 2 is a side view similar to FIG. 1, with the guide wire removed, and illustrating the follower in cross-section;

FIG. 3 is a side view similar to FIG. 1 illustrating the follower in cross-section and slidingly engaged with the guide wire;

DETAILED DESCRIPTION OF THE PREFERRED EMBODIMENT

Figure 4:
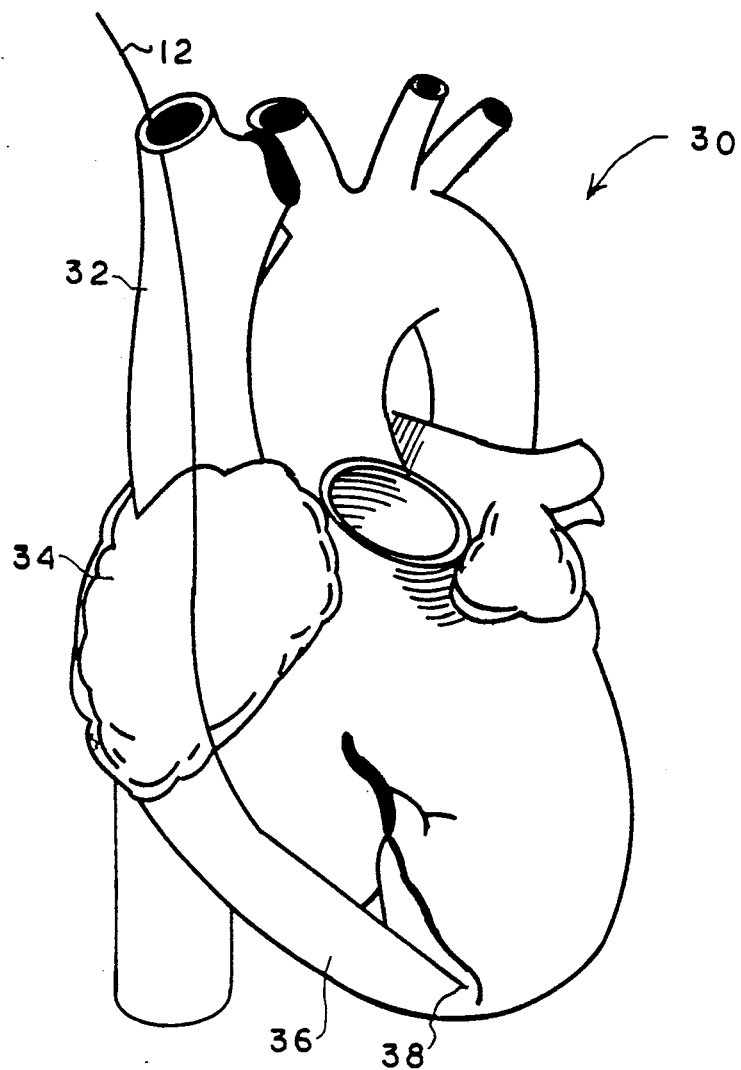
FIG. 4 is a prospective view of the human heart illustrating a guide wire which has been fed along a predetermined path into the right ventricle of the heart in implementing a first embodiment of the present invention.

Referring now to FIG. 1, it illustrates an arrangement 10 embodying the present invention to facilitate the implantation of an electrode of an endocardial or intravenous lead at an implantation site within or near the heart of the human body. The arrangement 10 generally includes a guide wire 12 and a lead means 14. The lead means 14 includes a proximal end 16, a distal end 18, and the electrode 20 to be implanted. The electrode 20 is formed of conductive material so that, when implanted, the electrode 20 may be utilized for sensing heart activity or delivering electrical energy to the heart.

In a manner well known in the art, the lead means 14 further includes an outer insulative sleeve 22 and a Plurality of conductive wires 24 for connecting electrode 20 and other electrodes which Might be carried by lead 14 to a connector (not shown) disposed at the proximal end 16 of the lead 14.

As may best be seen in FIG. 2, the electrode 20 is disposed at the distal end 18 of the lead 14. The electrode 20, and hence the lead 14, includes an integrally formed follower 26 which includes an elongated channel 28. The elongated channel 28 is substantially circular in cross-section and has an inner transverse dimension which is slightly greater in dimension than the outer transverse dimension of the guide wire 12. As a result, and as can best be seen in FIG. 3, because the elongated channel 28 has an inner transverse dimension slightly greater in dimension than the outer transverse dimension of the guide wire 12, the follower 26 is arranged for slidingly engaging the guide wire 12.

The guide wire 12 is preferably formed of flexible material so that, as will be seen hereinafter, it may be fed along a predetermined path within the body, which predetermined path includes the implantation site for the electrode 20. As will further be seen hereinafter, after the guide wire 12 is fed to extend along the predetermined path, the follower 26 is engaged with the guide wire 12 to permit the lead 14 to be guided along the predetermined path on the guide wire until the electrode 20 reaches the implantation site for the electrode. When the electrode 20 reaches the implantation site, the guide wire 12 may be retracted along the predetermined path causing the electrode 20 to remain and be implanted at the implantation site for electrode 20.

Figure 5:
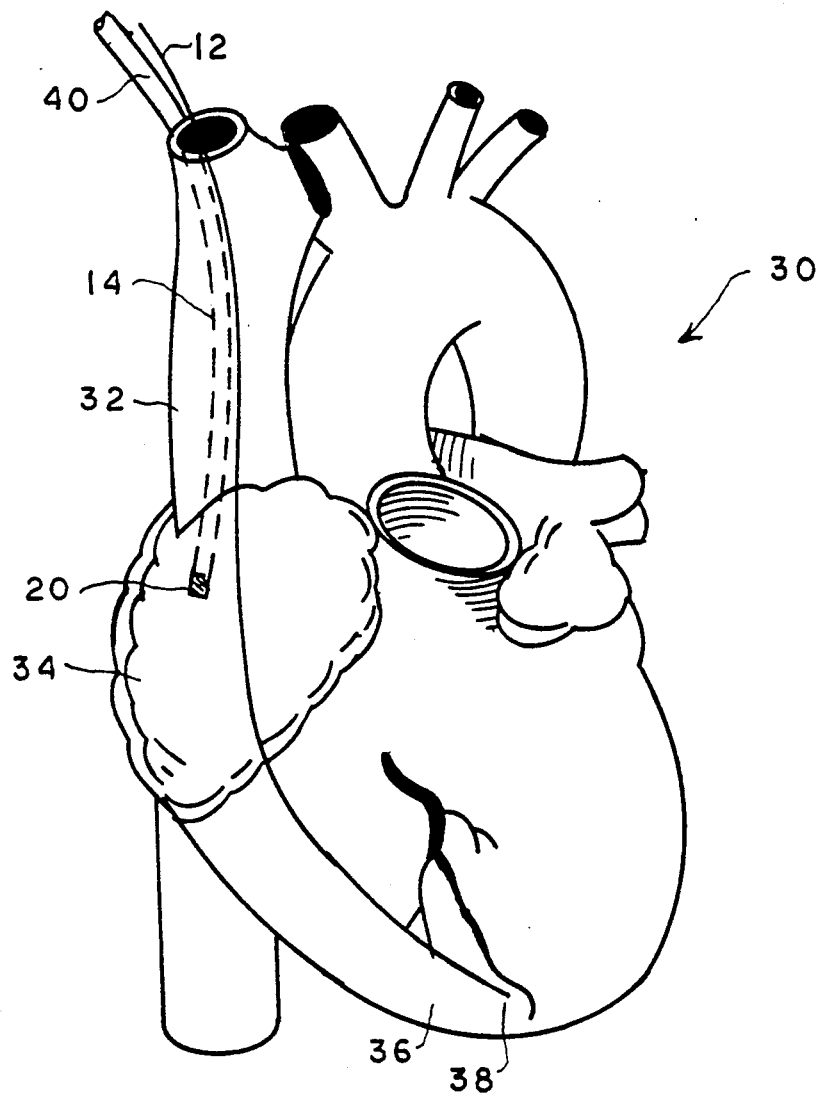
FIG. 5 is a prospective view of the human heart illustrating a lead being guided along the guide wire by an integrally formed follower in accordance with the first embodiment of the present invention.
Figure 6:
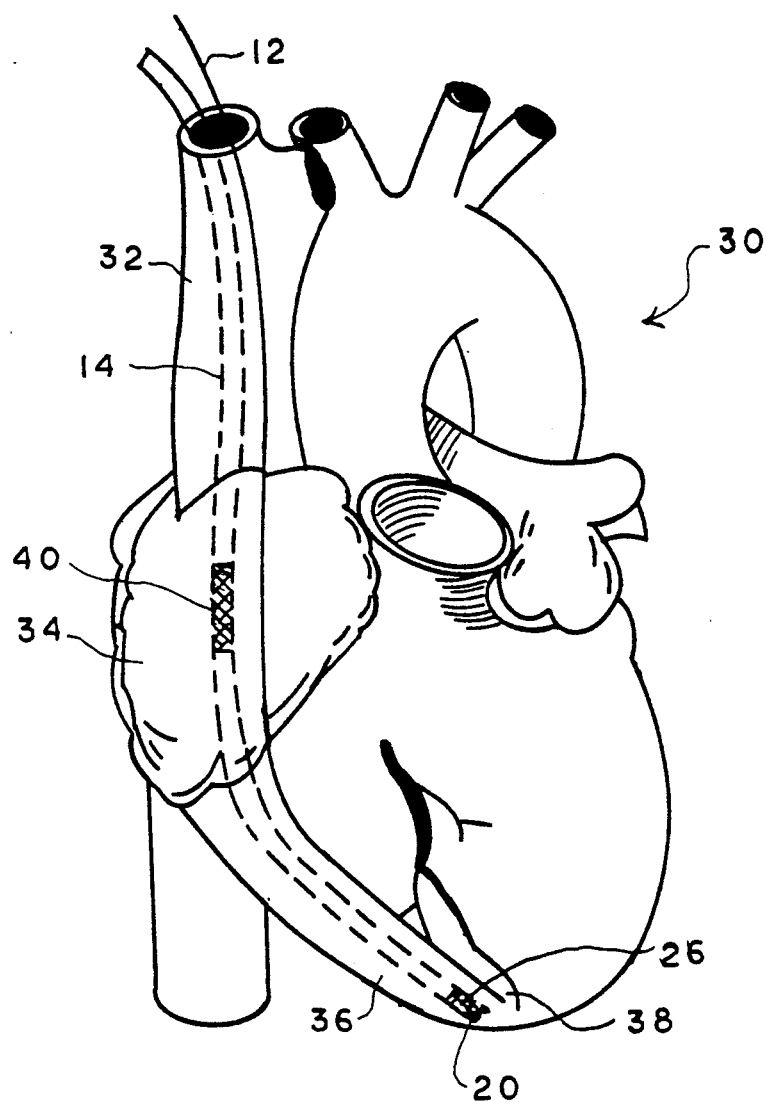
FIG. 6 is a prospective view of the human heart illustrating the lead at its final position with a distal electrode at an implantation site within the right ventricle of the heart and a proximal electrode at an implantation site within the right atrium of the heart in accordance with the first embodiment of the present invention.

FIGS. 4 through 6 illustrate the manner in which the arrangement 10 may be utilized to advantage when the lead 14 is utilized as an endocardial lead and the electrode 20 is to be implanted within a chamber of the heart. In accordance with this first embodiment, the electrode 20 is to be implanted within the right ventricle of the heart.

Referring to FIG. 4, it illustrates a human heart 30 in perspective view. The portions of the heart 30 of particular interest with respect to this first embodiment are the superior vena cava 32, the right atrium 34, and the right ventricle 36. The guide wire 12 has been fed along a predetermined path including the superior vena cava 32, the right atrium 34, and the right ventricle 36. The guide wire 12 has been fed along this predetermined path until the distal end 38 of guide wire 12 reaches the apex of the right ventricle 36 whereat the electrode 20 is to be implanted.

Referring now to FIG. 5, it illustrates the lead 14 at an intermediate position as it is guided along the guide wire 12 by the follower integrally formed within the electrode 20. To that end, the follower 26 (FIGS. 1 through 3) has been slidingly engaged on the guide wire 12 so that as the lead 14 is inserted into the heart 30, the lead 14 is guided along the predetermined path on the guide wire 12 through the superior vena cava 32 and into the right atrium 34.

As will also be noted in FIG. 5, the lead 14 carries another or proximal electrode 40. The proximal electrode 40 is elongated and, as will be seen in FIG. 6, the proximal electrode 40 is spaced from the distal electrode 20 so that, when the electrode 20 resides at the apex of the right ventricle 36, the proximal electrode 40 will reside within the right atrium 34 of the heart 30.

Referring now to FIG. 6, it can be seen that the lead 14 has been guided along the guide wire 12 so that electrode 20 has reached the distal end 38 of the guide wire 12 and thus resides at its implantation site within the right ventricle 36 at the apex of the right ventricle 36. Also, the proximal electrode 40 resides at its implantation site within the right atrium 34 of the heart 30. With electrode 20 residing at its implantation site within the right ventricle 36 and with the proximal electrode 40 residing at its implantation site within the right atrium 34, the guide wire 20 may now be retracted from the elongated channel of the integrally formed follower 26 and removed from the heart 30 along the predetermined path of the right ventricle 36, the right atrium 34, and the superior vena cava 32.

The lead 14 may find particular application with an implantable atrial defibrillator. In such an application, the electrode 20 is utilized for sensing heart activity within the right ventricle 36 of the heart 30 and the proximal electrode 40 may be utilized for sensing heart activity within the right atrium 34 of the heart 30 and as one of a pair of electrodes for delivering cardioverting electrical energy to the atria of the heart 30.

Figure 7:
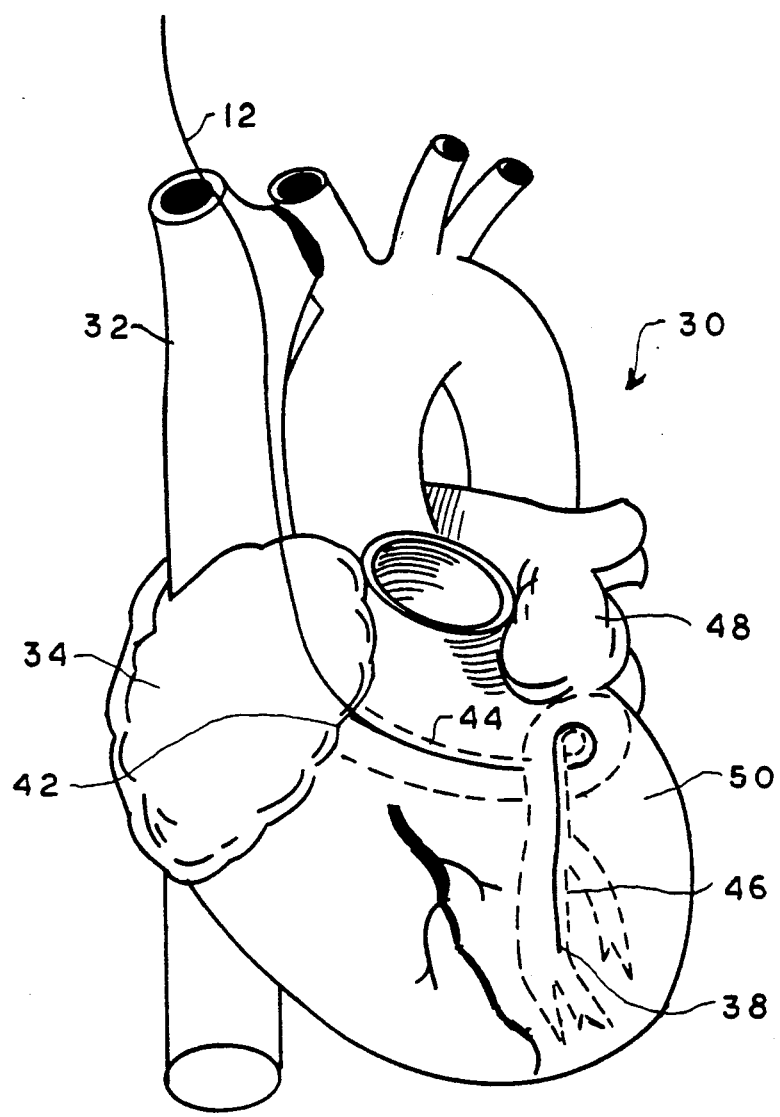
FIG. 7 is a prospective view of the human heart illustrating a guide wire which has been fed along a predetermined path into a coronary vein, such as the great vein, communicating with the coronary sinus of the heart to implement a second embodiment of the present invention.
Figure 8:
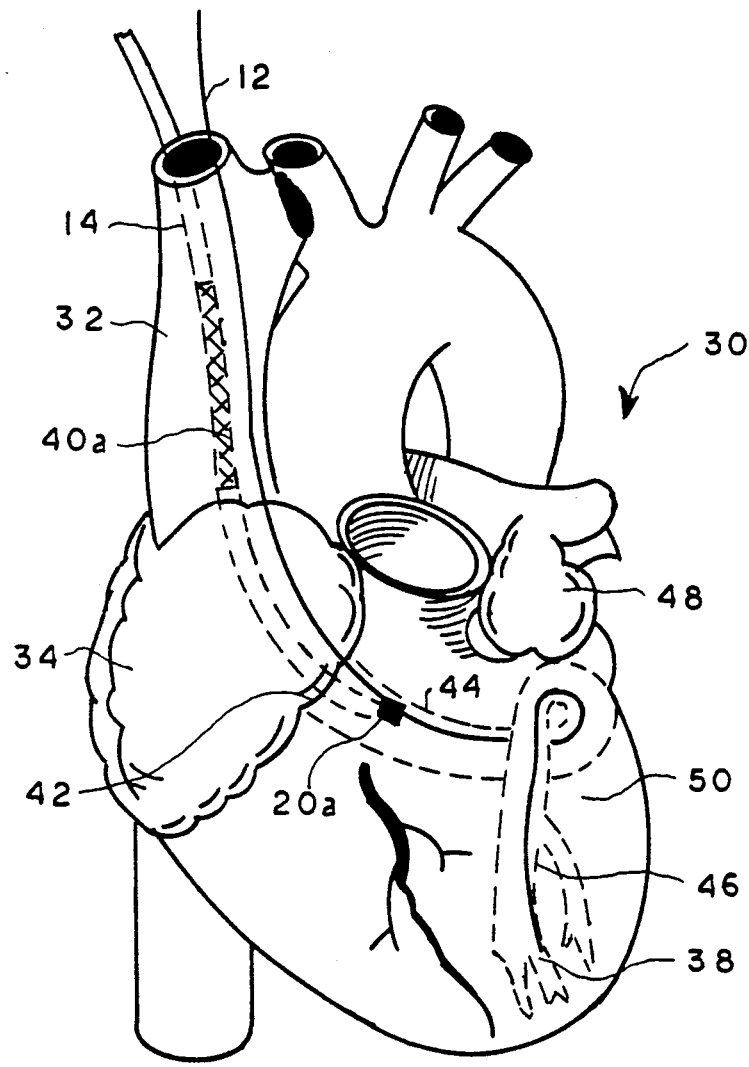
FIG. 8 is a prospective view of the human heart illustrating an intravenous lead being guided along the guide wire by an integrally formed follower in accordance with the second embodiment of the present invention.
Figure 9:
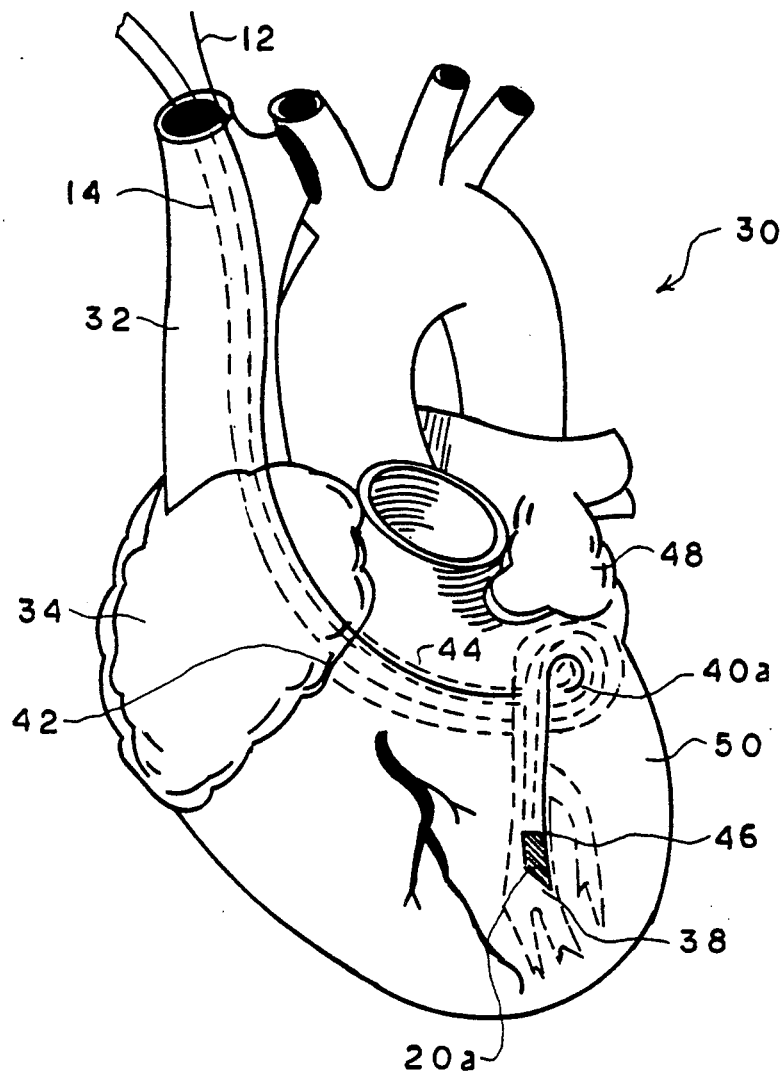
FIG. 9 is a prospective view of the human heart illustrating the intravenous lead at its final position with a distal electrode at an implantation site within the great vein and a proximal electrode at an implantation site within the coronary sinus of the heart.

FIGS. 7 through 9 illustrate the manner in which the arrangement 10 of the present invention may be utilized to advantage when the lead 14 is to be utilized as an intravenous lead and the electrode 20 (herein referred to as electrode 20a in this second embodiment) is to be implanted within a coronary vein such as the great vein of the heart. Referring more particularly to FIG. 7, it again illustrates, in perspective view, the heart 30. The portions of the heart illustrated in FIG. 7 which are of particular interest in accordance with this second embodiment are the superior vena cava 32, the right atrium 34, the valve of coronary sinus 42, the coronary sinus 44, the great vein 46, the left atrium 48, and the left ventricle 50, of the heart 30. As will be noted in FIG. 7, the guide wire 12 has been fed along a predetermined path within the heart including the superior vena cava 32, the right atrium 34, the valve of coronary sinus 42, the coronary sinus 44, and the great vein 46. The guide wire 12 has been so fed along the aforementioned predetermined path so that the distal end 38 of the guide wire 12 is well within the great vein 46.

Referring now to FIG. 8, it illustrates the lead 14 at an intermediate stage as it is being fed into the heart and guided along the aforementioned predetermined path on the guide wire 12. To that end, the integrally formed follower has been slidingly engaged with the guide wire 12 so that the lead 14 may be guided along the predetermined path on the guide wire 12. As will also be noted in FIG. 8, the lead 14 includes another or proximal electrode 40a. The electrode 40a is elongated in configuration and spaced from the distal electrode 20a such that when the distal electrode 20a reaches the distal end 38 of guide wire 12, well within the great vein 46, the proximal electrode 40a will reside in the coronary sinus 44 of the heart 30. As illustrated in FIG. 8, the intermediate stage of the feeding of lead 14 along guide wire 12 is such that the distal electrode 20a has just passed through the valve of coronary sinus 42 and has entered the coronary sinus 44.

Referring now to FIG. 9, it may be seen that the lead 14 has been guided along the guide wire 12 so that the distal electrode 20a has reached the distal end 38 of the guide wire 12. As a result, the distal electrode 20a resides at its implantation site well within the coronary sinus 46 and the proximal electrode 40a resides at its implantation site within the coronary sinus 44. As a result, the lead 14 has been fed along the predetermined path including the superior vena cava 32, the right atrium 34, the valve of coronary sinus 42, the coronary sinus 44, and into the great vein 46.

With the distal electrode 20a residing at its implantation site within the great vein 46 and with the proximal electrode 40a residing at its implantation site within the coronary sinus 44, the guide wire 12 may be retracted from the integrally formed follower and removed from the heart 30 in a reverse direction along the aforementioned predetermined path. This will cause the distal electrode 20a to remain at its implantation site within the great vein 46 and the proximal electrode 40a to remain at its implantation site within the coronary sinus 44. Because the coronary sinus 44 is closely adjacent to the left atrium 48 of the heart 30 and because the great vein 46 closely adjacent the left ventricle 50 of the heart 30, the lead 14 illustrated in FIG. 9 may be utilized to particular advantage with an implantable atrial defibrillator. In such an application, the distal electrode 20a within the great vein 46 may be utilized for sensing heart activity of the left ventricle 50 of the heart 30 and the proximal electrode 40a may be utilized for sensing heart activity of the left atrium 48 and as the second electrode of a pair of electrodes for delivering cardioverting electrical energy to the atria 34 and 48 of the heart 30. More specifically, and as disclosed in the aforementioned copending application Ser. No. 07/856,514, the proximal electrode 40 of FIG. 6 and the proximal electrode 40a of FIG. 9 may be utilized for delivering cardioverting electrical energy to the atria 34 and 48 of the heart. As a result, the cardioverting electrical energy is delivered between the right atrium 34 and the coronary sinus 44 closely adjacent the left atrium 48. This delivery path concentrates the cardioverting electrical energy to the atria 34 and 48 of the heart. The proximal electrode 40 of FIG. 6 and the proximal electrode 40a of FIG. 9 may also be utilized for sensing atrial activity of the heart to enable the determination as to whether atrial fibrillation is present within the heart. The distal electrode 20 of FIG. 6 and the distal electrode 20a of FIG. 9 may be utilized for sensing ventricular activity of the heart to enable a determination as to whether atrial fibrillation may be occurring and to enable the cardioverting electrical energy to be applied to the atria 34 and 48 of the heart in synchronism with an R wave detected in the ventricles 36 and 50 by the distal electrode 20 of FIG. 6 and the distal electrode 20a of FIG. 9.

The arrangement disclosed herein in accordance with the present invention to facilitate the implantation of an electrode of an endocardial or intravenous lead at an implantation site within the heart of a human exhibits a number of distinct advantages over the prior art. For example, since the follower, which slidingly engages the guide wire 12 to permit the guiding of the lead along the predetermined path defined by the path of the guide wire, is integrally formed with the lead, the arrangement of the present invention requires fewer manipulations by the physician during implantation and thus minimizes added complexity to the already complex procedure of implanting such leads and electrodes. In addition, the integrally formed follower does not require a separate carriage for guiding the lead along the guide wire. As a result, there is no need for retracting such a carriage from the heart once the lead and electrode or electrodes are implanted. In addition, the integrally formed follower does not require the bending of the lead to permit retraction of the guide wire. Since the guide wire is simply slidingly engaged within the elongated channel of the integrally formed follower, it need only be pulled in a reverse direction along the predetermined path for retraction. Still further, such ready retraction of the guide wire permits the electrodes to be in their final implantation positions when the guide wire is retracted thus negating the need to further position the electrodes after retraction of the guide wire. Lastly, since the follower may be integrally formed within the distal electrode, the follower itself serves a secondary function by being an integral part of the distal electrode for either sensing heart activity or delivering electrical energy to the heart.

While particular embodiments of the present invention have been shown and described, modifications may be made, and it is therefore intended to cover in the appended claims, all such changes and modifications which fall within the true spirit and scope of the invention.

What is claimed is:

1. An arrangement to facilitate the implantation of an electrode of an endocardial or intravenous lead at an implantation site within a human body, said arrangement comprising:
   a guide wire formed of flexible material and arranged to be fed along a predetermined path within the body, said predetermined path including said implantation site; and
   a lead formed of flexible material, said lead including a proximal end, a distal end, and an electrode to be implanted, said electrode to be implanted including follower means for slidingly engaging said guide wire whereby,
   after said guide wire is fed to extend along said predetermined path, said follower means is engaged with said guide wire to permit said lead to be guided along said predetermined path until said electrode to be implanted resides at said implantation site whereupon, said guide wire is retracted from said follower means and along said predetermined path to cause said electrode to be implanted to remain at said implantation site.

2. An arrangement as defined in claim 1 wherein said guide wire has an outer transverse dimension and wherein said follower means includes an elongated channel having an inner transverse dimension slightly greater in dimension than said outer transverse dimension of said guide wire.

3. An arrangement as defined in claim 1 wherein said electrode to be implanted is at said distal end of said lead.

4. An arrangement as defined in claim 3 wherein said guide wire has an outer transverse dimension and wherein said follower means includes an elongated channel having an inner transverse dimension slightly greater in dimension than said outer transverse dimension of said guide wire.

5. A method of implanting an electrode at an implantation site within a human body, said method comprising the steps of:
   providing a guide wire formed of flexible material;
   feeding said guide wire along a predetermined path within the body, said predetermined path including said implantation site;
   providing a lead formed of flexible material and including a proximal end, a distal end, an electrode to be implanted, and a follower integrally formed in said lead, said follower for slidingly engaging said guide wire;
   engaging said follower with said guide wire and sliding said lead on said guide wire along said predetermined path until said electrode to be implanted reaches said implantation site; and thereafter
   sliding said guide wire from engagement with said follower and retracting said guide wire from the body along said predetermined path.

6. A method as defined in claim 5 wherein said electrode to be implanted is at the distal end of said lead.

7. A method of implanting an electrode at an implantation site within a coronary vein of a human body having a coronary sinus communicating with the coronary vein, a superior vena cava, a right atrium, and a valve of coronary sinus, said method comprising the steps of:
   providing a guide wire formed of flexible material;
   feeding said guide wire along a predetermined path within the body, said predetermined path including the superior vena cava, the right atrium, the valve of coronary sinus, the coronary sinus, and said coronary vein communicating with the coronary sinus;
   providing a lead formed of flexible material and including a proximal end, a distal end, an electrode to be implanted, and a follower integrally formed in said lead, said follower for slidingly engaging said guide wire;
   engaging said follower with said guide wire and sliding said lead on said guide wire along said predetermined path until said electrode to be implanted reaches said implantation site; and thereafter sliding said guide wire from engagement with said follower and retracting said guide wire from the body along said predetermined path.

8. A method as defined in claim 7 wherein said electrode to be implanted is at the distal end of said lead.

9. An arrangement to facilitate the implantation of an electrode at an endocardial or intravenous lead at an implantation site within a human body, said arrangement comprising:

a guide wire formed of flexible material and arranged to be fed along a predetermined path within the body, said predetermined path including said implantation site; and a lead formed of flexible material, said lead including a proximal end, a distal end, and an electrode to be implanted, said lead further including follower means formed on said lead so as to be non-removable from said lead, said follower means for slidingly engaging said guide wire whereby, after said guide wire is fed to extend along said predetermined path, said follower means is engaged with said guide wire to permit said lead to be guided along said predetermined path until said electrode to be implanted resides at said implantation site whereupon, said guide wire is retracted from said follower means and along said predetermined path to cause said electrode to be implanted to remain at said implantation site.

10. An arrangement as defined in claim 9 wherein said lead includes said electrode to be implanted at said distal end of said lead.

11. An arrangement as defined in claim 10 wherein said electrode to be implanted includes said follower means.

12. An arrangement as defined in claim 11 wherein said guide wire has an outer transverse dimension and wherein said follower means includes an elongated channel having an inner transverse dimension slightly greater in dimension than said outer transverse dimension of said guide wire.

* * * * *